(12) United States Patent
Apffel, Jr. et al.

(10) Patent No.: US 6,649,908 B2
(45) Date of Patent: Nov. 18, 2003

(54) MULTIPLEXING CAPILLARY ARRAY FOR ATMOSPHERIC PRESSURE IONIZATION-MASS SPECTROMETRY

(75) Inventors: James A. Apffel, Jr., Mountain View, CA (US); Hongfeng Yin, San Jose, CA (US); Thomas P. Doherty, San Mateo, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 52 days.

(21) Appl. No.: 09/960,890

(22) Filed: Sep. 20, 2001

(65) Prior Publication Data

US 2003/0052269 A1 Mar. 20, 2003

(51) Int. Cl.[7] ................................................ H01J 49/04
(52) U.S. Cl. ..................................................... 250/288
(58) Field of Search ................................. 250/288, 282

(56) References Cited

U.S. PATENT DOCUMENTS

| | | | |
|---|---|---|---|
| 5,175,431 A | 12/1992 | Eisele et al. | 250/288 |
| 5,396,065 A | 3/1995 | Myerholtz et al. | 250/287 |
| 5,468,452 A | 11/1995 | Hagiwara | 422/70 |
| 5,495,108 A | 2/1996 | Apffel, Jr. et al. | 250/288 |
| 5,689,111 A | 11/1997 | Dresch et al. | 250/287 |
| 5,736,741 A | 4/1998 | Bertsch et al. | 250/288 |
| 5,750,988 A | 5/1998 | Apffel, Jr. et al. | 250/288 |
| 5,753,910 A | 5/1998 | Gourley et al. | 250/288 |
| 5,917,184 A | 6/1999 | Carson et al. | 250/288 |
| 5,962,851 A | 10/1999 | Whitehouse et al. | 250/288 |
| 5,965,883 A | 10/1999 | Lee et al. | 250/288 |
| 6,020,586 A | 2/2000 | Dresch et al. | 250/287 |
| 6,043,487 A | 3/2000 | Waki | 250/288 |
| 6,198,096 B1 | 3/2001 | Le Cocq | 250/287 |
| 6,326,616 B1 * | 12/2001 | Andrien, Jr. et al. | 250/288 |

OTHER PUBLICATIONS

Richard D. Oleschuk et al., "Analytical microdevices of mass spectrometry", trends in analytical chemistry, vol. 19, No. 6, 2000, pp. 379–388.

C. Eckers et al., "Accurate mass liquid chromatography/mass spectrometry on orthogonal acceleration time–offlight mass analyzers using switch between separate sample and reference sprays", Anal Chem, Aug. 15, 2000; 72(16):3683–8 [Abstract Only].

L. Jiang et al., "Development of multi–ESI–sprayer, multi-atmospheric–pressure–inlet mass spectrometry and its application to accurate mass measurement using time–offlight mass spectrometry", Anal Chem Jan. 1, 2000: 72(1):20–4 [Abstract Only]—2 pgs.

V. de Biasi et al., "High throughout liquid chromatography/mass spectrometric analyses using a novel multiplexed electrospray interface", Rapid Commun Mass Spectrom Jun. 1999:13(12):1165–1168 [Abstract Only].

Longfei Jiang and Mehdi Moini, "*Development of MultiES-I–Sprayer, Multi–Atmospheric–Pressure–inlet Mass Spectrometry and Its Application to Accurate Mass Measurement Using Time–of–Flight Mass Spectrometry,*" Analytical Chemical, vol. 72, No. 1, Jan. 1, 2000, pp. 20–24.

Bateman, Robert et al., "*Multiple LC/MS: Parallel and Simultaneous Analyses of Liquid Streams by LC/TOF Mass Spectrometry Using a Novel Eight–Way Interface,*" Proceedings of the 47th ASMS Conference on Mass Spectrometry and Allied Topics, Jun. 13–18, 1999, Dallas TX, pp. 2216–2217.

* cited by examiner

*Primary Examiner*—John R. Lee
*Assistant Examiner*—Phillip Johnston

(57) ABSTRACT

A transfer capillary and interface are provided that allow samples from multiple fluid streams to be introduced into a single mass analyzer. The transfer capillary has two or more channels and is placed between a first chamber, in which ions from the multiple fluid streams are generated, and a second chamber that is in fluid communication with a mass analyzer. The interface includes ionizers that generate ionized sample from each fluid stream and that direct the ionized sample toward the channels of the transfer capillary. The transfer capillary includes a multiplex selector that allows ions to flow through a selected subset of channels and sequentially changes which of the channels are included in the subset of channels through which ions flow.

20 Claims, 4 Drawing Sheets

MULTIPLEXING CAPILLARY ARRAY FOR ATMOSPHERIC PRESSURE IONIZATION-MASS SPECTROMETRY

BACKGROUND OF THE INVENTION

1. Field of the Invention

The present invention relates to an interface for transferring fluid streams into a mass spectrometer system. In particular, the present invention relates to a transfer capillary that allows multiple fluid streams to be monitored by a single mass analyzer.

2. Description of the Background

The combination of mass spectrometry (MS) and liquid chromatography (LC) is one of the most powerful methods available for analysis of chemical compounds and is widely used in chemical, environmental, pharmaceutical, and biological research. In a liquid chromatograph, a sample containing a mixture of compounds is pumped through a separation column in a liquid mobile phase. The components of the sample mixture are separated as they pass through the column, and the separated components emerge from the column one after another. A detector is connected to the fluid stream at the column exit to detect the components as they leave the column.

In a mass spectrometer, compounds are positively or negatively charged in an ionization source. The masses of the resultant ions are determined in a vacuum by a mass analyzer that measures the mass/charge (m/z) ratio of the ions. When used as a detector for a liquid chromatograph, a mass spectrometer can provide information on the molecular weight and chemical structure of each compound separated by the chromatograph, allowing identification of each of the components of the mixture.

FIG. 1 illustrates a conventional LC/MS instrument 100. The mass spectrometer 105 contains a special interface 107 to connect the MS 105 to the LC 110. Interface 107 is required because compounds exiting the LC column 112 are dissolved in a liquid solvent and are at atmospheric pressure, whereas the mass analyzer is operated under high vacuum and requires the compounds to be in the gas phase. The interface 107 includes an atmospheric pressure ionization chamber 120, a first stage vacuum chamber 123, and a second stage vacuum chamber 127. The first stage vacuum chamber 123 is typically held at a pressure around two orders of magnitude less than the atmospheric pressure chamber 120, and the second stage vacuum chamber 127 is typically held at a pressure two to four orders of magnitude less than the first stage chamber 123. Effluent leaving column 112 enters the atmospheric pressure chamber 120 through sprayer 130, which nebulizes and ionizes compounds as they exit the column.

Ions leaving sprayer 130 are directed or, depending on the orientation of sprayer 130, attracted toward an ion transfer capillary 132, which is positioned between the atmospheric pressure chamber 120 and a first stage vacuum chamber 123. Ions that enter the transfer capillary 132 are swept into the first vacuum chamber 123 in a stream of gas due to the pressure difference between chambers 120 and 123. The ions leave the transfer capillary 132 and pass through skimmer 140 or other equipment within the second vacuum 127 to focus and direct the ions to the mass analyzer 115. Mass analyzer 115 determines the m/z ratio of each ion.

In many instances, it is desirable to be able to use a singe mass spectrometer to analyze multiple inlet streams coming from multiple LC columns or other liquid phase sample sources. Mass spectrometers are typically more expensive than liquid chromatographs, and thus it is cheaper to use a single mass spectrometer as a detector for multiple LC systems. Furthermore, particularly if the mass analyzer is a time-of-flight instrument, mass spectral acquisition is much faster than LC separation. Therefore, it is possible for multiple LC systems, or multiple parallel streams from a single LC system, to be monitored by a single mass spectrometer effectively simultaneously. This approach is referred to as multiplexing analysis.

Multiplexing analysis for LC/MS has been accomplished by altering interface 107 to allow ions generated from each of the multiple inlet streams to sequentially enter the transfer capillary 132. Designs for such interfaces are described, for example, in Bateman et al., "Multiple LC/MS: Parallel and Simultaneous Analyses of Liquid Streams by LC/TOF Mass Spectrometry Using a Novel Eight-Way Interface," Proceedings of the 47$^{th}$ ASMS Conference on Mass Spectrometry and Allied Topics, Jun. 13–18, 1999, Dallas Tex., pp 2216–2217; Analytical Chemistry, 2000, volume 72, p. 22A; and Analytical Chemistry, 2000, volume 72, pp. 20–24. These interfaces may suffer from problems such as cross-contamination and possible cross-reaction between samples from different fluid streams; mechanical complexity that causes the interface to be expensive and fragile; and slow switching between fluid streams that prevents the effectively simultaneous monitoring of multiple streams.

SUMMARY

The embodiments of the present invention provide a transfer capillary and mass spectrometer interface that allow samples from multiple fluid streams to be introduced into a single mass analyzer and multiplexing analysis to be conducted. Switching between ionized samples generated by the different fluid streams is accomplished by the transfer capillary, which allows for fast switching between the fluid streams and reduces the possibility of cross-contamination between ionized samples.

The mass spectrometer interface includes a first chamber through which the multiple fluid streams enter and a second chamber that is in fluid communication with a mass analyzer. The interface includes ionizers connected to the multiple fluid streams. The ionizers generate ionized sample from each fluid stream within the first chamber and direct the ionized sample toward the inlets of a transfer capillary.

The transfer capillary forms a passageway between the first and second chambers. In one embodiment the transfer capillary has two or more inlets, each connected to inlet channels. The inlet channels merge into a single outlet channel that is connected to an outlet. The inlets of the transfer capillary are positioned within a first chamber and the outlet positioned within a second chamber. In another embodiment the transfer capillary has multiple channels, and each channel has an inlet located within the first chamber and an outlet located within the second chamber.

The transfer capillary includes a multiplex selector that allows ions to flow through a selected subset of the channels while retarding the flow of ions through the non-selected channels. The multiplex selector is capable of changing which of the channels are in the selected subset through which ions are allowed to flow. The multiplex selector may be a mechanical gate placed across the channels, a set of conductors that electrostatically control the ion flow, a skimmer with multiple openings surrounded by conductors which electrostatically control which skimmer opening is active, or a pair of electrodes placed between the channel outlets and a skimmer which electrostatically control which stream is directed into the skimmer opening.

The second chamber of the interface is held at a lower pressure than the first chamber. Ions pass through the transfer capillary under the control of the multiplex selector into the second chamber and on into the mass analyzer. The interface may also include a controller for synchronizing the operation of the mass analyzer and the multiplex selector.

DETAILED DESCRIPTION

Figure 1:
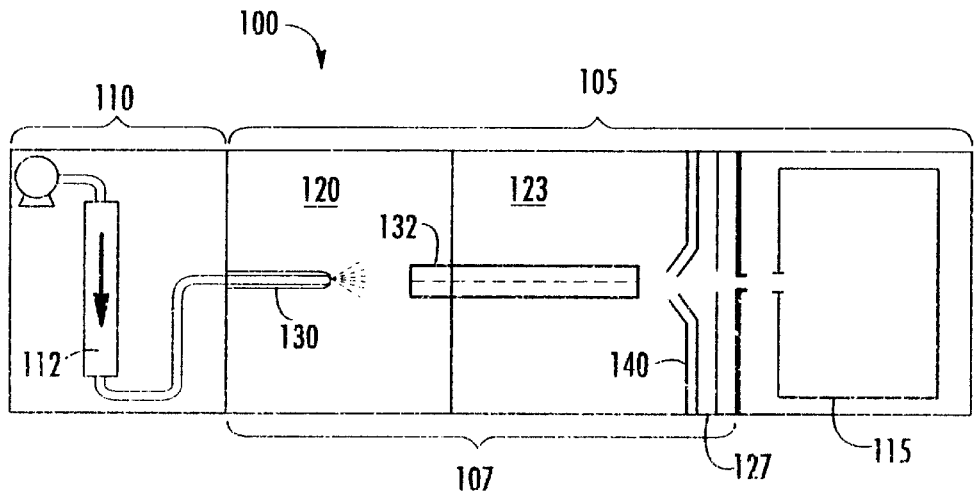
FIG. 1 is a diagram of an LC/MS system.
Figure 2:
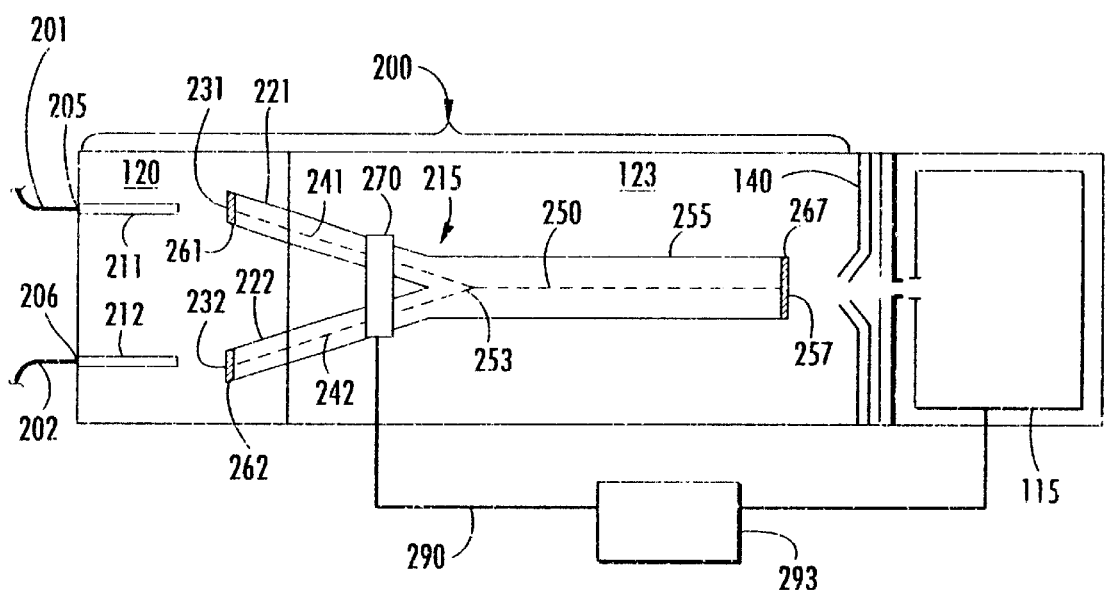
FIG. 2 is a sectional view of an MS interface and transfer capillary in accordance with an embodiment of the invention.

FIG. 2 illustrates an interface 200 that allows samples from multiple fluid streams to be analyzed in a single mass analyzer. Tubing 201, 202 conducts separate fluid streams into interface 200 through fluid inlet ports 205, 206. The tubing 201, 202 and fluid inlet ports 205, 206 may be connected to any fluid streams that contain sample to be analyzed by the mass analyzer 115. The fluid streams may be, for example, effluents pumped from a liquid chromatography system such as an HPLC, a micro-LC, or a capillary electrophoresis instrument. Although interface 200 is illustrated with two fluid streams in FIG. 2, interface 200 and its components may be expanded to accommodate any number of fluid streams.

The fluid streams are conducted from the fluid inlet ports 205, 206 through ionization devices, such as sprayers 211, 212, that nebulize and ionize the samples in the fluid streams. The ionized samples exit sprayers 211, 212 into the atmospheric pressure ionization chamber 120, and pass into transfer capillary 215.

Transfer capillary 215 forms a passage between the atmospheric pressure ionization chamber 120 and the first stage vacuum chamber 123, and can selectively transmit ionized samples from the individual fluid streams into chamber 123. In one embodiment, as illustrated in FIG. 2, transfer capillary 215 has inlet arms 221, 222 that each have inlets 231, 232 connected to inlet channels 241, 242. The channels 241, 242 of arms 221, 222 merge into a single outlet channel 250 at point 253. Outlet channel 250 extends through arm 255 to an outlet 257. Transfer capillary 215 may also have conductors 261, 262 located on the inlets 231, 232, and conductor 267 located on the outlet 257.

The inlets 231, 232 of transfer capillary 215 are located within atmospheric pressure chamber 120. Sprayers 211, 212 are positioned proximate to corresponding inlets 231, 232 so that ionized sample leaving each sprayer 211 or 212 only enters into one of the inlets, 231 or 232, respectively. To prevent ions that leave a sprayer 211, 212 from entering the wrong inlet, the arms 221, 222 and inlets 231, 232 of the transfer capillary are arranged so that the ion spray plumes leaving each sprayer 211, 212 do not cross paths. Cross-contamination of ions leaving sprayers 211, 212 may also be prevented by use of a shield (not shown) between sprayers 211, 212.

A potential applied to conductors 261, 262 attracts the ionized samples leaving sprayers 211, 212 to the respective inlets 231, 232. For example, if sprayers 211, 212 generate positive ions, a potential in the range of, e.g., −5 kV to −3.5 kV may be applied to conductors 261, 262 to attract the ions. The first vacuum chamber 123 is held at a much lower pressure, e.g., 10 torr, than the atmospheric pressure chamber 120. Thus, once inside the inlet channels 241, 242 of the transfer capillary, the ionized samples are entrained in a gas stream and swept toward the outlet 257 due to the pressure difference between chambers 120 and 123. Because of the multiple channels within transfer capillary 215, it may be necessary to use a greater pressure differential between chamber 120 and 123 than is conventionally used to create the necessary gas flow rate through the transfer capillary.

During operation, fluid streams enter interface 200 continuously, and sprayers 211, 212 continuously generate ions from samples in the fluid streams. The ionized samples are continuously sprayed into the atmospheric pressure chamber 120. To allow ionized samples from separate fluid streams to be delivered to the mass analyzer one at a time, transfer capillary 215 includes a multiplex selector, such as gate 270. The multiplex selector allows the separate ionized samples from each sprayer 211, 212 to sequentially pass through transfer capillary 215.

In the embodiment illustrated in FIG. 2, gate 270 is a mechanical device that allows ions to flow through a selected inlet channel, e.g., inlet channel 241, while blocking ion flow in the other inlet channel, e.g., inlet channel 242. Gate 270 sequentially switches open each inlet channel, to sequentially allow ionized samples from the sprayers 211, 212 to pass into the outlet channel 250. Exemplary embodiments of gate 270 and other multiplex selectors will be described below in relation to FIGS. 3A, 3B, 4A, and 4B.

The ions selected by the multiplex selector then pass from outlet channel 250, through outlet 257, and into chamber 123. At outlet 257, conductor 267 may have an applied potential, e.g., 100–300 V, to attract the sample ions and direct the ions to the next stage of vacuum. Sample ions leave outlet 257 and pass through skimmer 140 and additional components, such as ion guides and additional vacuum stages, that focus and accelerate the sample ions into a mass analyzer 115. Mass analyzer 115 produces a mass spectral signal for the sample ions.

As the multiplex selector sequentially switches open channels in transfer capillary 215, mass spectra of ionized sample from each fluid stream are sequentially collected. The spectral acquisition can be synchronized with the switching of the multiplex selector using, for example, control system 290. Control system 290 includes a controller 293 that can be circuitry or a computer processor, as understood by those of skill in the art, for coordinating the operation mass analyzer 115 and the multiplex selector 270.

If the mass spectral acquisition time is short enough, signals obtain from ionized samples generated by each sprayer 211, 212 can be observed virtually in parallel. One of the fastest mass analyzers currently available is the time-of-flight mass analyzer, which can acquire spectra at the rate of 10 to 100 per second. If mass analyzer 115 is a time-off-light mass analyzer, the orthogonal acceleration time-of-flight pulser is synchronized with the multiplex selector switching (with the appropriate delay to account for transit time to the mass analyzer). This synchronization is set so that the orthogonal packet pulsing of the mass analyzer is coincident with the arrival of ionized sample generated by a particular sprayer 211, 212 into the mass analyzer 115. In this case, controller 293 is a computer processor and includes system control, acquisition, and data processing software understood by those of skill in the art. In addition to controlling synchronization of the multiplex selector and mass analyzer, such software will correlate each signal obtained from the mass analyzer with the corresponding fluid stream and reconstruct the acquired spectra, so that the spectral acquisitions for each fluid stream appear to have been simultaneously collected (virtually parallel signals).

Figure 3A:
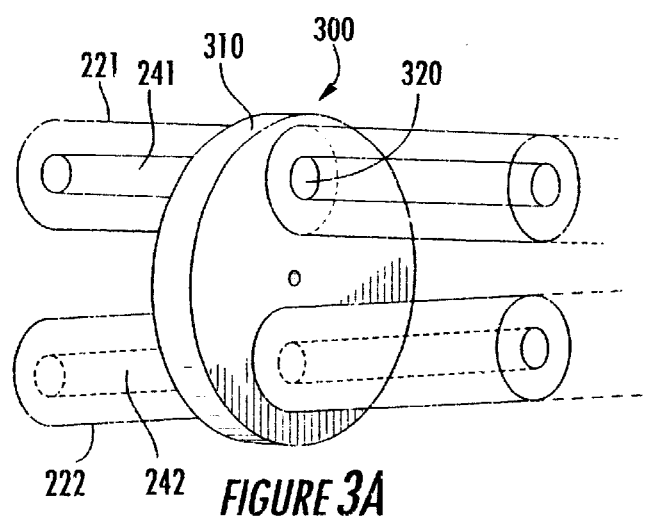
FIGS. 3A and 3B are perspective views of a mechanically operated multiplex selector.

FIG. 3 illustrates an exemplary mechanically operated multiplex selector, chopper 300, that can be used as the gate 270 illustrated in FIG. 2. In FIG. 3, chopper 300 has a plate 310 that is inserted cross-wise through the arms 221, 222 and corresponding inlet channels 241, 242. Plate 310 can be made of, e.g., metal or plastic. The plate 310 is vacuum sealed to the arms 221, 222 so that ions flowing through inlet channels 241, 242 do not leak out of transfer capillary 215 at the interface between the plate 310 and arms 221, 222. Plate 310 has an orifice 320 that can be positioned within arms 221 and aligned with the inlet channel 241, as shown in FIG. 3A. In the position illustrated in FIG. 3A, the plate 310 blocks the flow of ions through inlet channel 242.

Figure 3B:
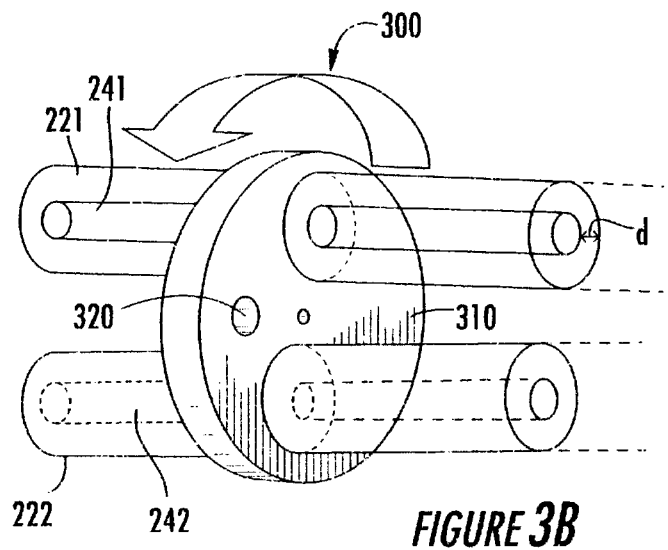

Plate 310 is attached to a support and actuator mechanism, such as a solenoid (not shown), that rotates plate 310. FIG. 3B illustrates plate 310 rotated so that orifice 320 is not aligned with either inlet channel 241, 242, and thus both inlet channels are blocked. Plate 310 may be continuously rotated so that orifice 320 is sequentially aligned with each of the inlet channels 241, 242, allowing ions from each of the sprayers 211, 212 to sequentially enter the outlet channel 250. The diameter of orifice 320 is smaller than the annular distance, d, between the inlet channel 241, 242 and the outer wall of arm 221, 222, so that the vacuum is not broken when the orifice is rotated across an inlet channel.

In other embodiments the multiplex selector operates by electrostatically controlling ion flow through transfer capillary 215. For example, electrostatic gating may be accomplished by appropriate biasing of the inlet conductors 261, 262. The conductors 261, 262 may be sequentially grounded, so that, for example, while conductor 261 is at −3.5 kV and, hence, ions from sprayers 211 are attracted to the inlet 231, conductor 262 is switched to ground, so that ions from sprayer 222 are not attracted to inlet 232 and are slowed or blocked from entering inlet channel 242. Then, the potentials applied to conductors 261, 262 are switched, and conductor 261 is grounded while conductor 262 is at −3.5 kV. Thus, the flow of ions into inlets 231, 232 is switched.

Figure 4A:
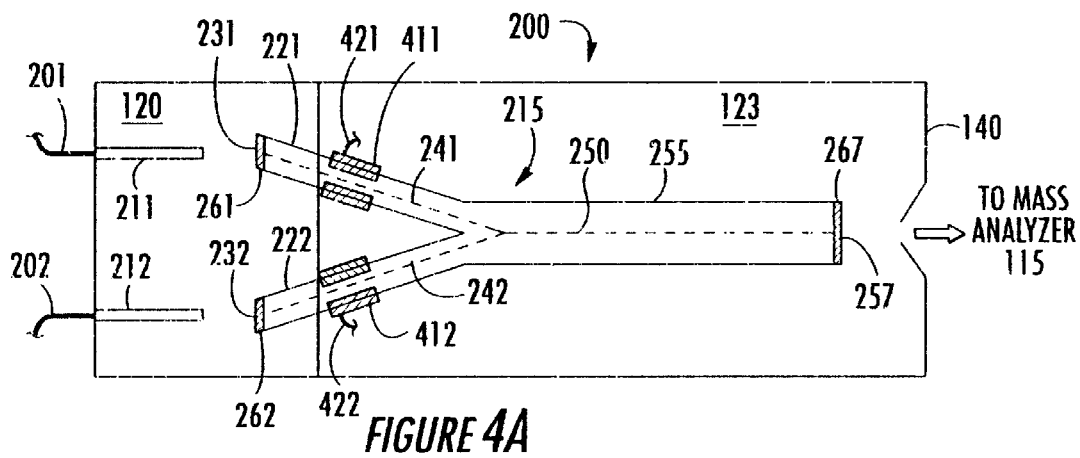
FIGS. 4A and 4B are sectional views of an MS interface and transfer capillary having an electrostatically operated multiplex selector.

A possible difficulty with sequentially grounding conductors 261 and 262, particularly if sprayers 211, 212 are electrospray ionizers, is that the spray plumes leaving sprayers 211, 212 are disrupted by the grounding. In another embodiment, as illustrated in FIG. 4A, an electrostatically operated multiplex selector may be operated without disrupting these spray plumes. Conductive sections 411, 412 are formed on each of the arms 221, 222 of the transfer capillary. Conductive sections 411, 412 may be, for example, metal rings or coils surrounding a section of each inlet channel 241, 242. Leads 421, 422 supply the conductive sections 411, 412, respectively. Upon application of a potential to the conductive sections 411, 412, a field is induced inside the capillary that can retard ion flow. The ionized sample is attracted to and strikes the surface of the charged conductive sections 411, 412, which stops the ions. In operation, one of the conductive sections, for example, conductive section 411, would have a potential set to allow ions to pass through channel 241. This potential may be optimized so that the ions are neither attracted or repelled under normal flow, or may be, e.g., ground or allowed to float. The other conductive section 412 would have, for the instance of positive ions being generated from sprayers 211, 212, a relatively high negative potential, so that the ions would be pulled to the inner surface of the channel 242. These potentials are sequentially switched, to sequentially allow ions to pass through the channels 241,242, into the outlet channel 250, and on to mass analyzer 115.

Figure 4B:
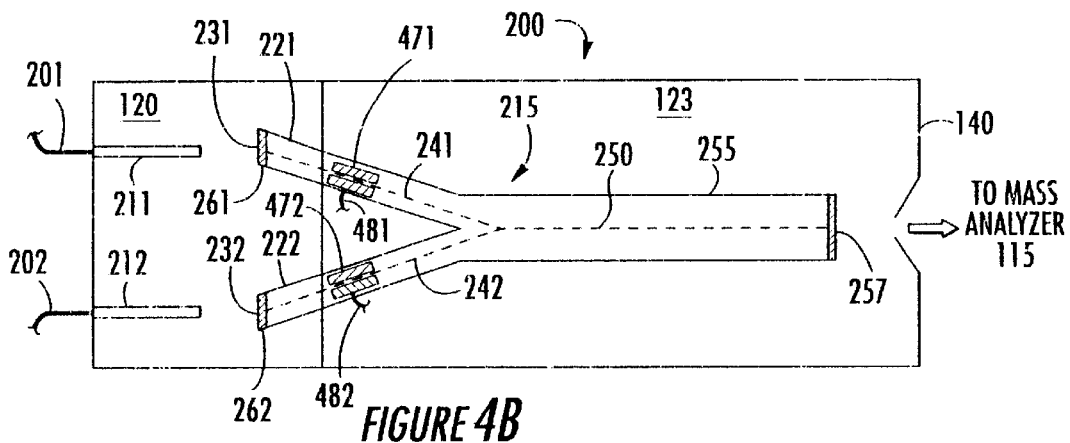

In another configuration, as illustrated in FIG. 4B, sections of the inner walls of the inlet channels 241, 242 are metalized with, for example, gold, nickel, or gold on nickel, to form conductive sections 471, 472. Conductive sections 471, 472 can be connected to a potential by leads 481, 482 that go through the wall of the arms 221, 222. Conductive sections 471, 472 can be sequentially biased, as described above for conductive sections 411, 412, to sequentially retard an ion stream in all but one of the inlet channels 241, 242, and select the ion stream that will pass into the outlet channel 250. The metalized inner wall sections may advantageously narrow the inner diameter of the inlet channel 241, 242, which may provide greater control over the flow rate of the ions through the conductive section 471, 472. Conductive sections 471, 472 may also be formed by cutting arms 221, 222 in half and inserting a metal capillary tube between the two halves.

FIGS. 5A–5D illustrate embodiments of transfer capillary 215 in which the channels in inlet arms 221, 222, instead of merging into a single outlet channel, proceed in separate channels 541, 542 through the single outlet arm 255. Because the channels 541, 542 never meet, cross-contamination of samples within transfer capillary 215 is prevented.

Figure 5A:
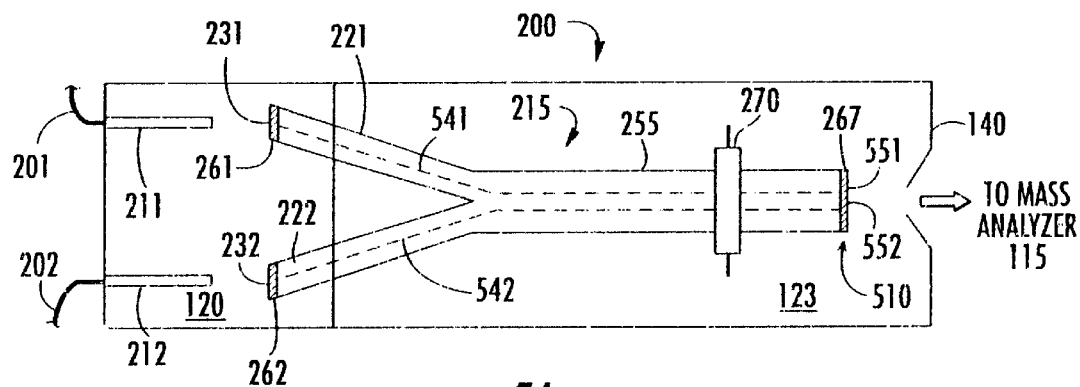
FIGS. 5A, 5B, 5C, and 5D illustrate an MS interface and a multiple channel transfer capillary in accordance with embodiments of the invention.

The embodiment shown in FIG. 5A allows a multiplex selector gate 270 (such as chopper 300 illustrated in FIG. 3) to be placed cross-wise through the transfer capillary 215 in the outlet arm 255, so gate 270 only crosses a single arm (arm 255) of the transfer capillary 215. Such a gate 270 may thus have a smaller overall diameter than the gate 270 illustrated in FIG. 2, and may be easier to implement.

Figure 5B:
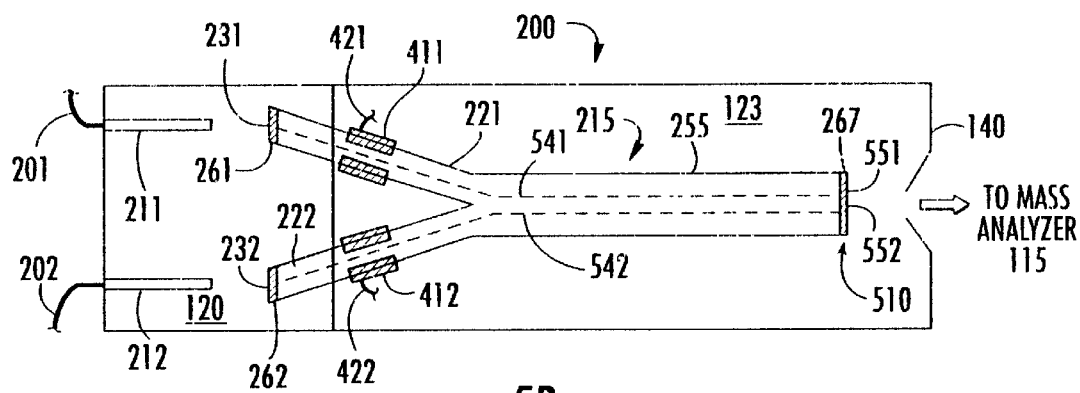

The embodiment shown in FIG. 5B, uses conductive sections 411, 412, located on the inlet arms 221, 222 to electrostatically control ion flow through the transfer capillary 215. Inner metalized conductive sections located on the inside wall of the channels may be placed at any point in the transfer capillary.

Figure 5C:
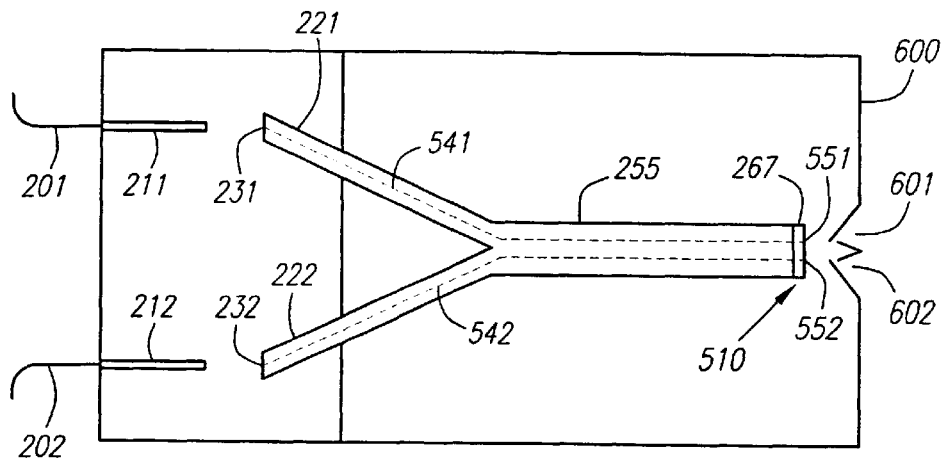

In the embodiment shown in FIG. 5C, skimmer 600 has multiple openings 601 and 602. Each skimmer opening 601 and 602 is aligned with one of channels 541 and 542. Skimmer openings 601 and 602 may be partially surrounded by a conductive material. By electrically biasing the appropriate skimmer opening, a single channel is selected and transferred to the mass analyzer.

Figure 5D:
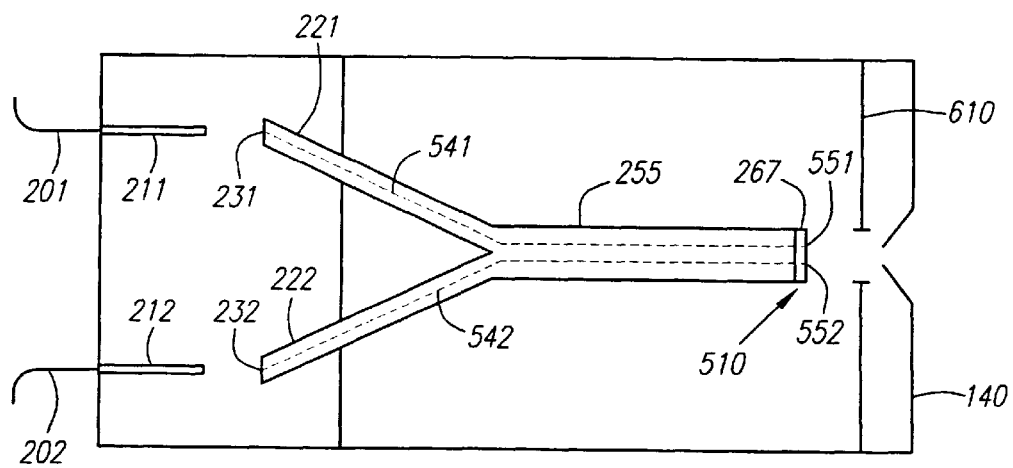

In the embodiment shown in FIG. 5D, electrodes 610 are placed between channel exits 551 and 552 and skimmer 140. Electrodes 610 do not physically block the flow from channels 541 and 542. Electrodes 610 are electrically biased to divert the spray direction. For example, in an embodiment where transfer capillary 215 has two channels 541 and 542, one bias state would divert the spray from channel exit 551 away from the skimmer opening while diverting the spray from channel exit 552 into the skimmer opening. The other bias state would reverse the selection of channel exits.

Arms 221, 222, and 255 of transfer capillary 215 are typically capillary tubing formed from a dielectric material such as glass. The total length of the transfer capillary, from inlets 231, 232 to outlet 257, is generally 5–20 cm, and typically 18 cm, the outer diameter of the capillary tubing is approximately 0.64 cm (0.25 inches), and the diameter of the channels is approximately 200 to 700 µm. In transfer capillary 215 of FIG. 2, in which the inlet channels 241, 242 merge into a single outlet channel 250, it may be necessary to tailor the internal diameter of the channels to balance gas flow and vacuum requirements. For instance, the inner diameter of the two inlet channels 241, 242 may be made half the inner diameter of the outlet channel 250 to ensure laminar flow through the transfer capillary 215.

Conductors 261, 262, and 267 are formed by plating the ends of the arms 221, 222, and 255 with a metal such as gold, nickel or gold on nickel. The conductors 261, 262, and 267 typically extend for approximately 1 cm down the outside of the arms, 221, 222, and 255, respectively.

Transfer capillary 215 may also be a microfluidic device formed using microfabrication techniques in which the channels are cut into a planar dielectric substrate using, for example, photolithographic, wet chemical etch, or micromachining techniques. A second planar substrate is then laid over and bonded to the first substrate. The diameters of channels in the microfabricated transfer capillary 215 are typically in the range of 0.1 µm to 500 µm. The multiplex selector could be, for instance, a miniature mechanical gate, or the channels could be metalized, by deposition of gold or nickel, to form an electrostatically operated multiplex selector.

Any ionization method may be used to ionize the sample in the fluid streams so long as the ions generated from each fluid stream are capable of entering inlets 231, 232 and do not become cross-contaminated. Typically, the sprayers 211, 212 illustrated in interface 200 are coaxial pneumatic nebulizers that utilize an electrospray method for ionization. In these sprayers a high electric field gradient at the end of a hollow needle charges the surface of the fluid stream as it passes through the needle, and a gas with a high flow rate passes through a hollow outer tube surrounding the needle to vaporize the liquid. Other possible ionization methods include atmospheric pressure chemical ionization and inductively coupled plasma.

Interface 200 is illustrated herein with sprayers 211, 212 arranged in a 180° orientation so the sprayers 211, 212 are facing inlets 231, 232 and ionized sample leaving the sprayers 211, 212 is aimed directly at the inlets 231, 232. Other orientations for sprayers may be used, so long as cross-contamination is prevented. Sprayers 211, 212 may, for example, have an orthogonal orientation with respect to inlets 231, 232, as described in U.S. Pat. Nos. 5,495,108 and 5,750,988, both issued to Apffel et al., and U.S. Pat. No. 5,736,741 issued to Bertsh et al., all incorporated herein by reference in their entirety. These patents also describe the design and construction of typical chambers 120 and 123.

Transfer capillary 215 is illustrated herein with two inlet arms, however, the number of inlet arms and channels may be expanded to any number to accommodate any number of fluid streams. If it is desired that spectral acquisition data for each fluid stream appears to be collected simultaneously, the number of inlet channels used, and hence, the number of fluid streams that can be monitored, may be limited by the acquisition speed of the mass analyzer. For a given acquisition speed, the number of channels must be small enough so that signal resulting from each fluid stream can be collected and reconstructed without introducing a delay in the appearance of the spectra for each stream.

When multiplex selector 215 has multiple inlet channels, a technique known as correlation chromatography, which is understood by those of skill in the art, may be used to increase the duty cycle through each channel. In this technique, groups of channels are simultaneously opened to let groups of ions pass through the transfer capillary at the same time. For example, a group of the conductive sections of an electrostatic multiplex selector, such as conductive sections 411, 412, can be grounded together to simultaneously open those channels. The ions that pass through the opened channels mix, and the result is an overlapped spectrum containing data on samples from the fluid streams corresponding to the group of inlet channels that was opened. The set of inlet channels that make up each group of channels opened is sequentially varied according to a pseudo-random pattern. The pseudo-random pattern enables the spectra of the grouped ions to overlap in a way that can be analyzed using known mathematical techniques to extract the individual spectra corresponding to samples from each fluid stream. Methods for deconvoluting overlapped spectra generated by such pseudo-random sequences are described, for example, in U.S. Pat. No. 6,198,096 to Le Cocq, incorporated herein by reference in its entirety.

While particular embodiments of the present invention have been shown and described, it will be obvious to those skilled in the art that changes and modifications may be made without departing from this invention in its broader aspects. For example, in the embodiment illustrated in FIG. 2, the point 253 at which the inlet channels merge may be located within arm 255, at, e.g., the mid-point of arm 255, closer to outlet 257. This would allow a mechanical multiplex selector, such as gate 270 illustrated in FIG. 5A, to be placed cross-wise through the outlet arm 255, before the inlet channels merge. Therefore, the appended claims are to encompass within their scope all such changes and modifications as fall within the scope of this invention.

What is claimed is:

1. An apparatus for introducing a sample from a fluid streams into a mass analyzer comprising:

a first chamber;

a second chamber having a lower pressure than said first chamber and in fluid communication with said mass analyzer;

a transfer capillary having two inlets located within said first chamber, said two inlets each in fluid communication with two inlet channels, said two inlet channels in fluid communication with an outlet channel, said outlet channel in fluid communication with an outlet, said outlet located within said second chamber;

a multiplex selector that allows ions to flow from a selected subset of said two inlet channels into said outlet channel and out of said outlet, and that is capable of changing the set inlet channels comprising said selected subset; and two or more ionizers in fluid communication with said two fluid streams, wherein said ionizers generate ionized sample within said first chamber and direct said ionized sample into corresponding inlets of said transfer capillary.

2. The apparatus of claim 1, wherein said multiplex selector comprises a plate having an orifice, and wherein said plate crosses said two inlet channels and can be rotated so that said orifice is aligned with said selected subset of inlet channels.

3. The apparatus of claim 1, wherein said multiplex selector comprises two conductors, each conductor surrounding a section of said two inlet channels, wherein ion flow through inlet channels not included in said selected subset is retarded by application of a potential to conductors surrounding sections of said inlet channels not included in said selected subset.

4. The apparatus of claim 3, wherein said two conductors comprise a metal layer adhered to sections of inner walls of each of said two inlet channels.

5. The apparatus of claim 3, wherein said two inlet channels are surrounded by a dielectric material and said conductors surround said dielectric material.

6. The apparatus of claim 1, wherein said multiplex selector comprises conductors attached to said inlets and wherein a first potential is applied to a first set of conductors attached to inlets in fluid communication with said selected subset of inlet channels, and a second potential applied to a second set of conductors attached to inlets in fluid communication with inlet channels not included in said selected subset, and wherein said first potential attracts ionized sample and said second potential does not attract ionized sample.

7. The apparatus of claim 1, wherein said apparatus further includes a control system connected to said mass analyzer and said multiplex selector, and wherein said control system synchronizes operation of said multiplex selector and said mass analyzer.

8. The apparatus of claim 1, wherein said transfer capillary is a microfluidic device.

9. An apparatus for introducing a sample from a fluid stream into a mass analyzer comprising:
  a first chamber;
  a second chamber having a lower pressure than said first chamber and in fluid communication with said mass analyzer;
  a transfer capillary having two channels, each channel having an inlet located within said first chamber and an outlet located within said second chamber;
  a multiplex selector that allows ions to flow through a selected subset of said two channels and that is capable of changing the set of channels comprising said selected subset, and
  two ionizers in fluid communication with said two fluid streams, wherein said ionizers generate ionized sample within said first chamber and direct said ionized sample into corresponding inlets of said transfer capillary.

10. The apparatus of claim 9, wherein said multiplex selector comprises a plate having an orifice, and wherein said plate crosses said two channels and can be rotated so that said orifice is aligned with said selected subset of channels.

11. The apparatus of claim 9, wherein said multiplex selector comprises two conductors, each conductor surrounding a section of said two channels, wherein ion flow through channels not included in said selected subset is retarded by application of a potential to conductors surrounding sections of said channels not included in said selected subset.

12. The apparatus of claim 11, wherein said two conductors comprise a metal layer adhered to sections of inner walls of each of said two inlet channels.

13. The apparatus of claim 11, wherein said two inlet channels are surrounded by a dielectric material and said conductors surround said dielectric material.

14. The apparatus of claim 9, wherein said multiplexer selector comprises two electrodes, each electrode being adjacent to one of said channel outlets.

15. The apparatus of claim 9, wherein said multiplex selector comprises a skimmer positioned adjacent to said channel outlets, said skimmer comprising two openings, each opening aligned with one of said channel outlets, each opening being partially surrounded by a conductor.

16. A method for introducing two or more samples from two or more fluid streams into a mass analyzer comprising:
  ionizing said two or more samples within a first chamber having a first pressure;
  directing each of said two or more ionized samples toward corresponding inlets of a transfer capillary, wherein said inlets are in fluid communication with inlet channels, said inlet channels are in fluid communication with an outlet channel, said outlet channel is in fluid communication with an outlet and said outlet is located within a second chamber, said second chamber in fluid communication with said mass analyzer and said second chamber having a second pressure, wherein said second pressure is less than said first pressure thereby causing said two or more ionized samples to flow through said inlet channels; and
  retarding flow through a selected subset of said inlet channels using a multiplex selector within said transfer capillary such that a subset of said two or more ionized samples are retained within said transfer capillary, and wherein said multiplex selector is capable of changing the set of inlet channels comprising said selected subset.

17. The method of claim 16 further comprising changing the set of inlet channels comprising said selected subset.

18. The method of claim 17 further comprising synchronizing the changing of the set of inlet channels comprising said selected subset with collection of data by said mass analyzer.

19. A method for introducing two or more samples from two or more fluid streams into a mass analyzer comprising:
  ionizing said two or more samples within a first chamber having a first pressure;
  directing each of said two or more ionized samples into corresponding inlets, wherein each of said inlets is in fluid communication with a channel, each of said channels is in fluid communication with an outlet, and each outlet is located within a second chamber, said second chamber in fluid communication with said mass analyzer and said second chamber having a pressure less than said first chamber thereby causing said two or more ionized samples to flow through said channels; and
  retarding flow through a selected subset of said channels using a multiplex selector within said transfer capillary such that a subset of said two or more ionized samples are retained within said transfer capillary, and wherein said multiplex selector is capable of changing the set of channels comprising said selected subset.

20. The method of claim 19 further comprising:
  changing the set of channels comprising said subset; and
  synchronizing the changing of the set of channels comprising the selected subset with collection of data by said mass analyzer.

* * * * *